(12) United States Patent
Vaughan

(10) Patent No.: US 9,273,018 B2
(45) Date of Patent: Mar. 1, 2016

(54) PIPERAZINE DERIVATIVES

(75) Inventor: Keith Vaughan, Halifax (CA)

(73) Assignee: St. Mary's University (CA)

( * ) Notice: Subject to any disclaimer, the term of this patent is extended or adjusted under 35 U.S.C. 154(b) by 0 days.

(21) Appl. No.: 14/238,717

(22) PCT Filed: Aug. 10, 2012

(86) PCT No.: PCT/CA2012/000747
§ 371 (c)(1),
(2), (4) Date: May 22, 2014

(87) PCT Pub. No.: WO2013/023273
PCT Pub. Date: Feb. 21, 2013

(65) Prior Publication Data
US 2014/0309196 A1  Oct. 16, 2014

Related U.S. Application Data

(60) Provisional application No. 61/522,955, filed on Aug. 12, 2011.

(51) Int. Cl.
C07D 295/30  (2006.01)
C07D 401/06  (2006.01)
C07D 213/74  (2006.01)

(52) U.S. Cl.
CPC ............ *C07D 295/30* (2013.01); *C07D 213/74* (2013.01); *C07D 401/06* (2013.01)

(58) Field of Classification Search
CPC .......................... C07D 295/30; C07D 401/06
See application file for complete search history.

(56) References Cited

PUBLICATIONS

STN (CAS) Database accession No. 906627-64-3, "Piperazine, 1-[2-(2-chlorophenyl)diazenyl]-4-phenyl", Entered STN: Sep. 14, 2006.
International Search Report and Written Opinion from related PCT Patent Application No. PCT/CA2012/000747 mailed Nov. 1, 2012, application now published as WO2013/023273 on Feb. 21, 2013.
Kohlbach, "O nekim derivatima piperazina s he-moterapeutskim djelovanjem", Arhiv Za Hemiju I Farmaciju, pp. 99-123 (1937) *Croation Language Only.*
Prelog Nad Kohlbach, "Sur les colorants N-pipérazylés. Colorants azoïques I", Collection of Czechoslovak Chemical Communications, Part 5, pp. 377-389 (1936) *French Language Only.*
Tonelli et al, "Antiviral and cytotoxic activities of aminoarylazo compounds and aryltriazene derivatives", Bioorganic & Medicinal Chemistry, vol. 17, No. 13, pp. 4425-4440 (2009).

*Primary Examiner* — Robert Havlin
(74) *Attorney, Agent, or Firm* — Susan T. Evans; McDermott Will & Emery LLP

(57) ABSTRACT

Disclosed are piperazine derivatives having the general formula: (I) Also disclosed are methods of treating a subject having cancer with this compound or a pharmaceutical composition comprising the compound.

(I)

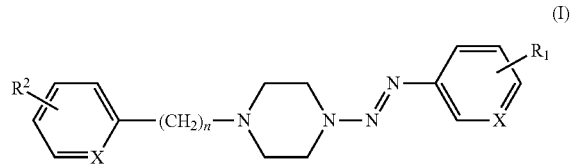

11 Claims, 3 Drawing Sheets

PIPERAZINE DERIVATIVES

CROSS-REFERENCE TO RELATED APPLICATIONS

This application is a U.S. National Stage of International Patent Application No. PCT/CA2012/000747, filed Aug. 10, 2012, which claims the benefit of priority to U.S. Provisional Patent Application No. 61/522,955, filed Aug. 12, 2011, the content each of which is incorporated herein by reference in its entirety.

FIELD OF THE INVENTION

The invention generally relates to anti-cancer agents. More specifically, the invention relates to piperazine derivatives.

BACKGROUND OF THE INVENTION

Temozolomide is an oral alkylating agent that has been in use since the turn of the century for the treatment of aggressive brain tumors.

Temozolomide is thought to alkylate/methylate deoxyribonucleic acid (DNA) at the N-7 and O-6 positions of guanine (Newlands E S et al., Cancer Treatment Reviews 23:35-61, 1997). This methylation is believed to act as a trigger for apoptosis, which ultimately results in lesions in the DNA and death of the cancer cells. In some tumor cells, the effectiveness of temozolomide is limited by the presence of O-6-methylguanine-DNA methyltransferase (MGMT) or O-6-alkylguanine-DNA alkyltransferase (AGT or AGAT) in the cells. These enzymes are part of the cell-repair machinery of a cell and can reverse the methylation caused by temozolomide.

Since tumor cells that synthesize the MGMT/AGT enzyme are more resistant to killing by temozolomide, various researchers have investigated whether the inclusion of O-6-benylguanine (O6-BG), an inhibitor of MGMT, would be able to overcome this resistance and improve the drug's therapeutic effectiveness. In the laboratory, this combination indeed showed increased activity in tumor cell culture in vitro and in animal models in vivo (Ueno et al., Mol. Cancer Ther. 5(3):732-8, 2006). However, a recently completed phase II clinical trial with brain tumor patients yielded mixed outcomes; while there was some improved therapeutic activity when 06-BG and temozolomide were given to patients with temozolomide-resistant anaplastic glioma, there seemed to be no significant restoration of temozolomide sensitivity in patients with temozolomide-resistant glioblastoma multiforme (Quinn et al., J. Clin. Oncol., 27(8):1262-1267, 2009). As such, the effectiveness of temozolomide in the treatment of cancers could be improved.

SUMMARY OF THE INVENTION

According to an aspect of the present invention, there is provided a compound represented by the general formula (I):

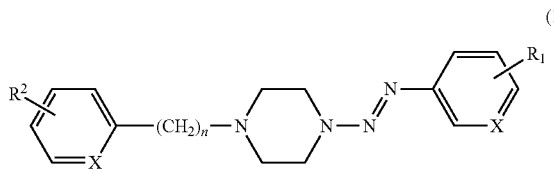

(1)

wherein n is 0, 1 or 2;
X is CH or N;
R1 represents hydrogen, an alkyl group, halogen, an ether, cyano, pyridyl, $COCR_3$, $CO_2R_4$, $CONH_2$, $NO_2$, or CF;
R2 represents one or more substituents selected from the group consisting of halogen, alkyl, pyridyl, cyano, acetyl, phenyl and phenyl substituted with alkyl;
R3 represents an alkyl group or $CONH_2$; and
R4 represents an alkyl group.

In one embodiment, R1 represents a member selected from the group consisting of:
para-nitro; para-cyanide, para-chloride, para-bromide, para-methyl, ortho-bromide, para-methyl ether, meta-trifluoromethyl, hydrogen, para-ethyl ester, para-methyl ester, para-acetyl and 3-pyridyl.

In another embodiment, R2 represents a member selected from the group consisting of:
hydrogen, para-chloride, meta-, para-dichloride, ortho-methyl, para-fluoride, para-acetyl, 2-pyridyl, ortho-cyanide, and meta-, ortho-methyl.

In a further embodiment, n=1;
R1 represents a member selected from the group consisting of:
para-nitro; para-cyanide, para-bromide, para-methyl, hydrogen, para-methyl ether and para-methyl ester; and
R2 represents a member selected from the group consisting of:
para-methyl, ortho-methyl and meta-methyl.

In a yet further embodiment, N=2;
R1 represents para-methyl ester; and
R2 represents hydrogen.

According to another aspect of the present invention, there is provided a compound selected from the group consisting of:
a) 1-[(E)-2-(4-nitrophenyl)diazen-1-yl]-4-phenylpiperazine;
b) 4-[(E)-2-(4-phenylpiperazin-1-yl)diazen-1-yl]benzonitrile;
c) Methyl 4-[(E)-2-(4-phenylpiperazin-1-yl)diazen-1-yl]benzoate;
d) 1-{4-[(E)-2-(4-phenylpiperazin-1-yl)diazen-1-yl]phenyl}ethan-1-one;
e) 1-[(E)-2-(4-chlorophenyl)diazen-1-yl]-4-phenylpiperazine;
f) 1-[(E)-2-(4-bromophenyl)diazen-1-yl]-4-phenylpiperazine;
g) 1-[(E)-2-(4-methylphenyl)diazen-1-yl]-4-phenylpiperazine;
h) 1-[(E)-2-(4-methoxyphenyl)diazen-1-yl]-4-phenylpiperazine;
i) 1-[(E)-2-(2-bromophenyl)diazen-1-yl]-4-phenylpiperazine;
j) 1-(4-chlorophenyl)-4-[(E)-2-(4-nitrophenyl)diazen-1-yl]piperazine;
k) 4-[(E)-2-[4-(4-chlorophenyl)piperazin-1-yl]diazen-1-yl]benzonitrile;
l) methyl 4-[(E)-2-[4-(4-chlorophenyl)piperazin-1-yl]diazen-1-yl]benzoate;
m) 1-[(E)-2-(4-bromophenyl)diazen-1-yl]-4-(4-chlorophenyl) piperazine;
n) 1-(4-chlorophenyl)-4-[(E)-2-(4-methylphenyl)diazen-1-yl]piperazine;
o) 1-(4-chlorophenyl)-4-[(E)-2-(4-methoxyphenyl)diazen-1-yl]piperazine;
p) 1-(3,4-dichlorophenyl)-4-[(E)-2-(4-nitrophenyl)diazen-1-yl]piperazine;
q) 4-[(E)-2-[4-(3,4-dichlorophenyl)piperazin-1-yl]diazen-1-yl]benzonitrile;

r) 1-[(E)-2-(4-bromophenyl)diazen-1-yl]-4-(3,4-dichlorophenyl)piperazine;
s) 1-(3,4-dichlorophenyl)-4-[(E)-2-(4-methylphenyl)diazen-1-yl]piperazine;
t) 1-(3,4-dichlorophenyl)-4-[(E)-2-(4-methoxyphenyl)diazen-1-yl]piperazine;
u) 1-(3,4-dichlorophenyl)-4-[(E)-2-[3-(trifluoromethyl)phenyl]diazen-1-yl]piperazine;
v) 1-{4 [(E)-2-[4-(3,4-dichlorophenyl)piperazin-1-yl]phenyl}ethan-1-one;
w) 1-(2-methylphenyl)-4-[(E)-2-(4-nitrophenyl)diazen-1-yl]piperazine;
x) 4-[(E)-2-[4-(2-methylphenyl)piperazin-1-yl]diazen-1-yl]benzamide;
y) ethyl 4-[(E)-2-[4-methylphenyl)piperazin-1-yl]diazen-1-yl]benzoate;
z) 1-[(E)-2-(4-chlorophenyl)diazen-1-yl]-4-(2-methylphenyl) piperazine;
aa) 1-[(E)-2-(4-methoxyphenyl)diazen-1-yl]-4-(2-methylphenyl) piperazine;
bb) 1-(2-methylphenyl)-4-[(E)-2-phenyldiazen-1-yl]piperazine;
cc) 1-{4-[(E)-(2-methylphenyl)piperazin-1-yl]diazen-1-yl]phenyl}ethan-1-one;
dd) 1-[(E)-2-(4-bromophenyl)diazen-1-yl]-4-(4-fluorophenyl) piperazine;
ee) 1-(4-fluorophenyl)-4-[(E)-2-(4-methylphenyl)diazen-1-yl]piperazine;
ff) methyl 4-[(E)-2-[4[(4-fluorophenyl)piperazin-1-yl]diazen-1-yl]benzoate;
gg) 1-(4-{4-[(E)-2-(4-bromophenyl)diazen-1-yl)piperazin-1-yl}phenyl)ethan-1-one;
hh) 1-(4-{4-[(E)-2-(4-methylphenyl)diazen-1-yl)piperazin-1-yl}phenyl)ethan-1-one;
ii) methyl 4-[(E)-2-[4-(4-acetylphenyl)piperazin-1-yl]diazen-1-yl]benzoate;
jj) 1-(4-{4-[(E)-2-(4-nitrophenyl)diazen-1-yl)piperazin-1-yl}phenyl)ethan-1-one;
kk) 4-[(E)-2-[4-(4-acetylphenyl)piperazin-1-yl]diazen-1-yl]benzonitrile;
ll) ethyl 4-[(E)-2-[4-(4-acetylphenyl)piperazin-1-yl]diazen-1-yl]benzoate;
mm) 1-(4-{4-[(E)-2-phenyldiazen-1-yl)piperazin-1-yl}phenyl)ethan-1-one;
nn) 1-[(E)-2-(4-nitrophenyl)diazen-1-yl]-4-(pyridine-2-yl) piperazine;
oo) 4-[(E)-2-[pyridin-2-yl)piperazin-1-yl]diazen-1-yl]benzonitrile;
pp) methyl 4-[(E)-2-[4-(pyridin-2-yl)piperazin-1-yl]diazen-1-yl]benzoate;
qq) 1-[(E)-2-(4-bromophenyl)diazen-1-yl]-4-(pyridin-2-yl) piperazine;
rr) 1-[(E)-2-(4-methylphenyl)diazen-1-yl]-4-(pyridin-2-yl) piperazine;
ss) 1-{2-[(E)-4-[pyridine-2-yl)piperazine-1-yl]diazen-1-yl] phenyl}ethan-1-one;
tt) 1-[(E)-2-(2-bromophenyl)diazen-1-yl]-4-(pyridin-2-yl) piperazine;
uu) 1-[(E)-2-(3-pyridyl)diazen-1-yl]-4-(pyridin-2-yl)piperazine;
vv) 1-[(E)-2-phenyldiazen-1-yl]-4-(pyridin-2-yl)piperazine;
ww) 2-{4-[(E)-2-(4-bromophenyl)diazen-1-yl]piperazin-1-yl}benzonitrile;
xx) 2-{4-[(E)-2-(4-methylphenyl)diazen-1-yl]piperazin-1-yl}benzonitrile;
yy) methyl 4-[(E)-2-[4-(2-cyanophenyl)piperazin-1-yl]diazen-1-yl]benzoate;
zz) 2-{4-[(E)-2-(4-methoxyphenyl)diazen-1-yl]piperazin-1-yl}benzonitrile;
aaa) 1-(2,3-dimethylphenyl)-4-[(E)-2-(4-nitrophenyl)diazen-1-yl]piperazine
bbb) 4-[(E)-2-[4-(2,3-dimethylphenyl)piperazin-1-yl]diazen-1-yl]benzonitrile;
ccc) methyl 4-[(E)-2-[4-(2,3-dimethylphenyl) piperazin-1-yl]diazen-1-yl]benzoate;
ddd) 1-[(E)-2-(4-bromophenyl)diazen-1-yl]-4-(2,3-dimethylphenyl) piperazine;
eee) 1-(2,3-dimethylphenyl)-4-[(E)-2-(4-methylphenyl)diazen-1-yl]piperazine;
fff) 1-(2,3-dimethylphenyl)-4-[(E)-2-phenyldiazen-1-yl]piperazine;
ggg) 1-[(E)-2-(4-chlorophenyl)diazen-1-yl]-4-(2,3-dimethylphenyl) piperazine;
hhh) 1-(2,3-dimethylphenyl)-4-[(E)-2-(4-methoxyphenyl) diazen-1-yl]piperazine;
iii) 1-[(4-methylphenyl)methyl]-4-[(E)-2-(4-nitrophenyl) diazen-1-yl]piperazine;
jjj) 4-[(E)-2-{4-[(4-methylphenyl)methyl]piperazin-1-yl}diazen-1-yl]benzonitrile;
kkk) methyl 4-[(E)-2-{4-[(4-methylphenyl)methyl]piperazin-1-yl}diazen-1-yl]benzoate;
lll) 1-[(E)-2-(4-bromophenyl)diazen-1-yl]-4-[(4-methylphenyl)methyl]piperazine;
mmm) 1-[(E)-2-(4-methylphenyl)diazen-1-yl]-4-[(4-methylphenyl)methyl]piperazine;
nnn) 1-[(4-methylphenyl)methyl]-4-[(E)-2-phenyldiazen-1-yl]piperazine;
ooo) 1-[(3-methylphenyl)methyl]-4-[(E)-2-(4-nitrophenyl) diazen-1-yl]piperazine;
ppp) 4-[(E)-2-{4-[(3-methylphenyl)methyl]piperazin-1-yl}diazen-1-yl]benzonitrile;
qqq) methyl 4-[(E)-2-{4-[(3-methylphenyl)methyl]piperazin-1-yl}diazen-1-yl]benzoate;
rrr) 1-[(E)-2-(4-bromophenyl)diazen-1-yl]-4-[(3-methylphenyl)methyl]piperazine;
sss) 1-[(E)-2-(4-methylphenyl)diazen-1-yl]-4-[(3-methylphenyl)methyl]piperazine;
ttt) 1-[(2-methylphenyl)methyl]-4-[(E)-2-(4-nitrophenyl) diazen-1-yl]piperazine;
uuu) 4-[(E)-2-{4-[(2-methylphenyl)methyl]piperazin-1-yl}diazen-1-yl]benzonitrile;
vvv) methyl 4-[(E)-2-{4-[(2-methylphenyl)methyl]piperazin-1-yl}diazen-1-yl]benzoate;
www) 1-[(E)-2-(4-bromophenyl)diazen-1-yl]-4-[(2-methylphenyl)methyl]piperazine;
xxx) 1-[(E)-2-(4-methylphenyl)diazen-1-yl]-4-[(2-methylphenyl)methyl]piperazine;
yyy) 1-[(2-methylphenyl)methyl]-4-[(E)-2-phenyldiazen-1-yl]-4-piperazine; and
zzz) methyl 4-[(E)-2-[4-(2-phenylethyl)piperazin-1-yl]diazen-1-yl]benzoate According to a further aspect of the present invention, there is provided a method of treating a subject having cancer comprising administering a therapeutic effective amount of a compound of general formula I to the subject in need thereof.

In one embodiment, the cancer is selected from the group consisting of glioblastomas, lung cancers and colon cancers.

According to another aspect of the present invention, there is provided use of a compound of general formula I for the treatment of a cancer.

According to a further aspect of the present invention, there is provided use of a compound of general formula I in the preparation of a medicament for the treatment of a cancer.

In one embodiment, the cancer is selected from the group consisting of glioblastomas, lung cancers, and colon cancers.

According to an aspect of the present invention there is provided a pharmaceutical composition comprising the compound of general formula I and a pharmaceutically acceptable carrier.

BRIEF DESCRIPTION OF THE DRAWINGS

These and other features, aspects and advantages of the present invention will become better understood with regard to the following description and accompanying drawings wherein.

DETAILED DESCRIPTION OF THE INVENTION

Figure 1:
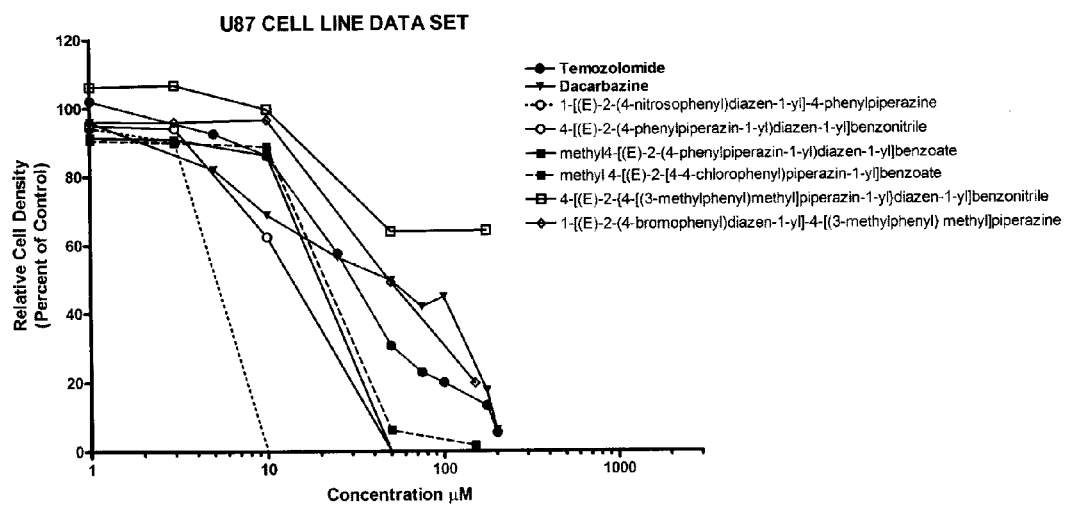
FIG. 1 is a graphical representation of the relative cell density of U87MG glioblastoma cells exposed to varying concentrations of temozolomide, dacarbazine, 1-[(E)-2-(4-nitrophenyl)diazen-1-yl]-4-phenylpiperazine, 4-[(E)-2-(4-phenylpiperazin-1-yl)diazen-1-yl]benzonitrile, methyl 4-[(E)-2-(4-phenylpiperazin-1-yl)diazen-1-yl]benzoate, methyl 4-[(E)-2-[4-(4-chlorophenyl)piperazin-1-yl)diazen-1-yl]benzoate; 1-[(E)-2-(4-bromophenyl)diazen-1-yl]-4-[(3-methylphenyl)methyl]piperazine, and 4-[(E)-2-{4-[(3-methylphenyl)methyl]piperazin-1-yl}diazen-1-yl]benzonitrile.

The following description is of a preferred embodiment by way of example only and without limitation to the combination of features necessary for carrying the invention into effect.

A compound represented by the general formula (I):

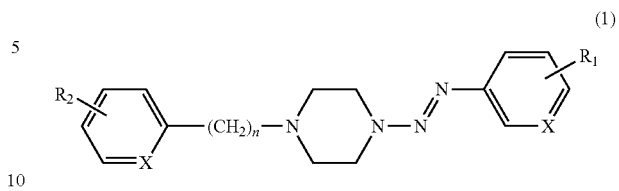

(1)

wherein n is 0, 1 or 2; X is CH or N; R1 represents hydrogen, an alkyl group, halogen, an ether, cyano, pyridyl, $COCR_3$, $CO_2R_4$, $NO_2$, or $CF_3$; R2 represents one or more substituents selected from the group consisting of halogen, alkyl, pyridyl, cyano, acetyl, phenyl and phenyl substituted with alkyl; R3 represents an alkyl group or $NH_2$; and R4 represents an alkyl group.

In one embodiment of the invention, the compound of general formula I preferably has R1 representing a member selected from the group consisting of: para-nitro; para-cyanide, para-chloride, para-bromide, para-methyl, ortho-bromide, para-methyl ether, meta-carbon trifluoride, meta-trifluoromethyl, hydrogen, para-ethyl ester, para-methyl ester, para-acetyl and 3-pyridyl.

In another embodiment, the compound of general formula I preferably has R2 representing a member selected from the group consisting of: hydrogen, para-choride, meta-, para-dichloride, ortho-methyl, para-floride, para-acetyl, 2-pyridyl, ortho-cyanide, and meta-, ortho-methyl.

In another embodiment, when the compound of general formula I has n=1; R1 represents a member selected from the group consisting of: para-nitro; para-cynide, para-bromide, para-methyl, hydrogen, para-methyl ether and para-methyl ester; and R2 represents a member selected from the group consisting of: para-methyl, ortho-methyl and meta-methyl.

In a further embodiment, when the compound of general formula I has n=2; R1 represents para-methyl ester; and R2 represents hydrogen.

For the purposes of the present invention halogen represents fluorine, chlorine, bromine or iodine.

An alkyl group, for the purposes of this disclosure, is broadly defined as a univalent saturated, straight or branched hydrocarbon chain. The hydrocarbon chain preferably containing from about one to eighteen carbon atoms ($C_{1-18}$-alkyl), more preferred from about one to eight carbon atoms ($C_{1-8}$-alkyl; lower alkyl), including pentyl, isopentyl, neopentyl, tertiary pentyl, hexyl and isohexyl. In an embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may be methy, ethyl, propyl or isopropyl.

An alkoxy group designates an "alkyl-O-" group, wherein alkyl is as defined above.

Examples of compounds that are represented by the general formula I, include, without limitation are shown in Table 1.

TABLE 1

| | Chemical name | Structure |
|---|---|---|
| 1 | 1-[(E)-2-(4-nitrophenyl)diazen-1-yl]-4-phenylpiperazine | 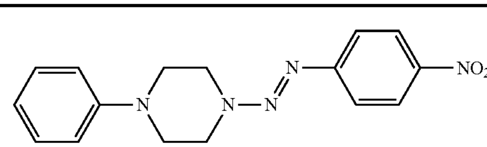 |

TABLE 1-continued

| | Chemical name | Structure |
|---|---|---|
| 2 | 4-[(E)-2-(4-phenylpiperazin-1-yl)diazen-1-yl]benzonitrile | 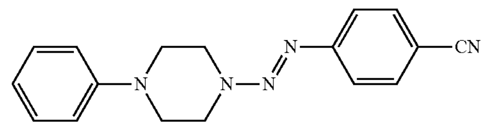 [SMILES: N#Cc1ccc(/N=N/N2CCN(c3ccccc3)CC2)cc1] |
| 3 | Methyl 4-[(E)-2-(4-phenylpiperazin-1-yl)diazen-1-yl]benzoate | 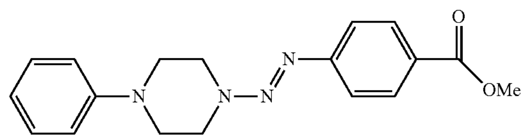 [SMILES: COC(=O)c1ccc(/N=N/N2CCN(c3ccccc3)CC2)cc1] |
| 4 | 1-{4-[(E)-2-(4-phenylpiperazin-1-yl)diazen-1-yl]phenyl}ethan-1-one | 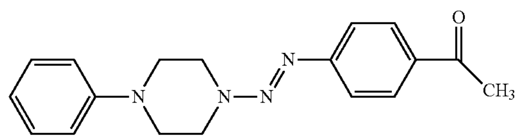 [SMILES: CC(=O)c1ccc(/N=N/N2CCN(c3ccccc3)CC2)cc1] |
| 5 | 1-[(E)-2-(4-chlorophenyl)diazen-1-yl]-4-phenylpiperazine | 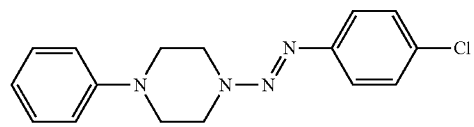 [SMILES: Clc1ccc(/N=N/N2CCN(c3ccccc3)CC2)cc1] |
| 6 | 1-[(E)-2-(4-bromophenyl)diazen-1-yl]-4-phenylpiperazine | 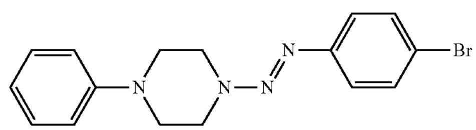 [SMILES: Brc1ccc(/N=N/N2CCN(c3ccccc3)CC2)cc1] |
| 7 | 1-[(E)-2-(4-methylphenyl)diazen-1-yl]-4-phenylpiperazine | 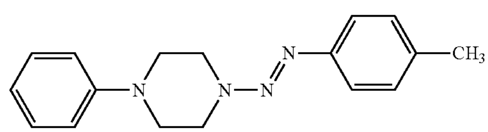 [SMILES: Cc1ccc(/N=N/N2CCN(c3ccccc3)CC2)cc1] |
| 8 | 1-[(E)-2-(4-methoxyphenyl)diazen-1-yl]-4-phenylpiperazine | 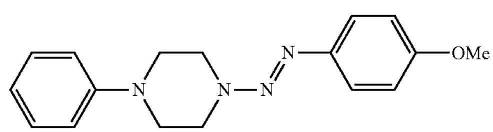 [SMILES: COc1ccc(/N=N/N2CCN(c3ccccc3)CC2)cc1] |
| 9 | 1-[(E)-2-(2-bromophenyl)diazen-1-yl]-4-phenylpiperazine | 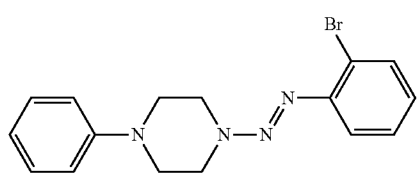 [SMILES: Brc1ccccc1/N=N/N1CCN(c2ccccc2)CC1] |
| 10 | 1-(4-chlorophenyl)-4-[(E)-2-(4-nitrophenyl)diazen-1-yl]piperazine | 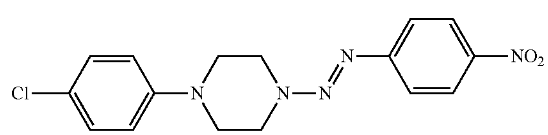 [SMILES: O=[N+]([O-])c1ccc(/N=N/N2CCN(c3ccc(Cl)cc3)CC2)cc1] |
| 11 | 4-[(E)-2-[4-(4-chlorophenyl)piperazin-1-yl]diazen-1-yl]benzonitrile | 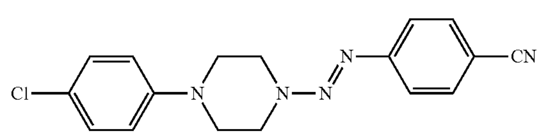 [SMILES: N#Cc1ccc(/N=N/N2CCN(c3ccc(Cl)cc3)CC2)cc1] |
| 12 | methyl 4-[(E)-2-[4-(4-chlorophenyl)piperazin-1-yl]diazen-1-yl]benzoate; | 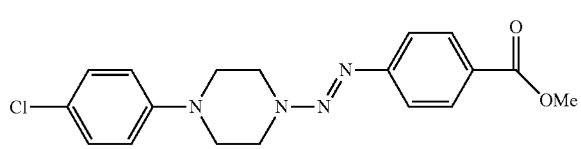 [SMILES: COC(=O)c1ccc(/N=N/N2CCN(c3ccc(Cl)cc3)CC2)cc1] |

TABLE 1-continued

| | Chemical name | Structure |
|---|---|---|
| 13 | 1-[(E)-2-(4-bromophenyl)diazen-1-yl]-4-(4-chlorophenyl)piperazine | 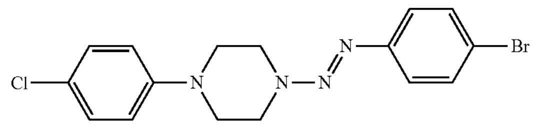 [SMILES: Clc1ccc(N2CCN(/N=N/c3ccc(Br)cc3)CC2)cc1] |
| 14 | 1-(4-chlorophenyl)-4-[(E)-2-(4-methylphenyl)diazen-1-yl]piperazine | 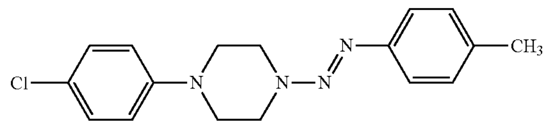 |
| 15 | 1-(4-chlorophenyl)-4-[(E)-2-(4-methoxyphenyl)diazen-1-yl]piperazine | 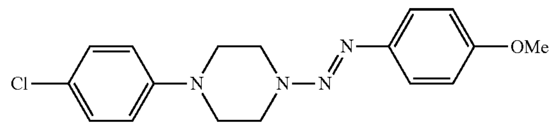 [SMILES: COc1ccc(/N=N/N2CCN(c3ccc(Cl)cc3)CC2)cc1] |
| 16 | 1-(3,4-dichlorophenyl)-4-[(E)-2-(4-nitrophenyl)diazen-1-yl]piperazine | 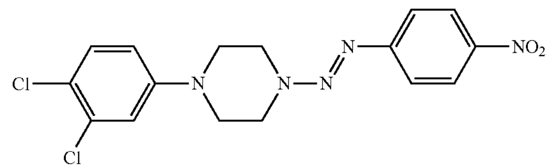 [SMILES: O=[N+]([O-])c1ccc(/N=N/N2CCN(c3ccc(Cl)c(Cl)c3)CC2)cc1] |
| 17 | 4-[(E)-2-[4-(3,4-dichlorophenyl)piperazin-1-yl]diazen-1-yl]benzonitrile | 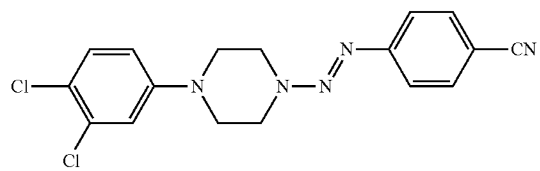 [SMILES: N#Cc1ccc(/N=N/N2CCN(c3ccc(Cl)c(Cl)c3)CC2)cc1] |
| 18 | 1-[(E)-2-(4-bromophenyl)diazen-1-yl]-4-(3,4-dichlorophenyl)piperazine | 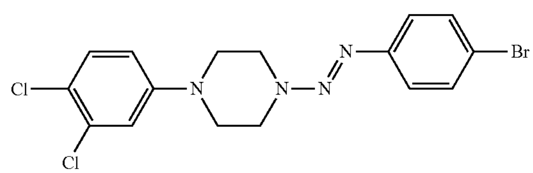 [SMILES: Clc1ccc(N2CCN(/N=N/c3ccc(Br)cc3)CC2)cc1Cl] |
| 19 | 1-(3,4-dichlorophenyl)-4-[(E)-2-(4-methylphenyl)diazen-1-yl]piperazine | 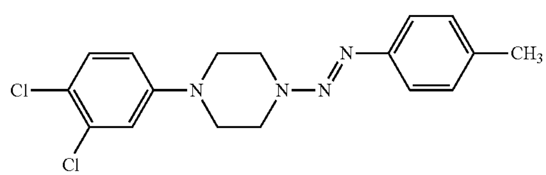 [SMILES: Cc1ccc(/N=N/N2CCN(c3ccc(Cl)c(Cl)c3)CC2)cc1] |
| 20 | 1-(3,4-dichlorophenyl)-4-[(E)-2-(4-methoxyphenyl)diazen-1-yl]piperazine | 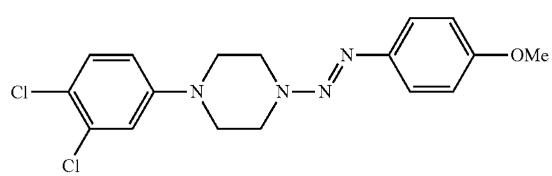 [SMILES: COc1ccc(/N=N/N2CCN(c3ccc(Cl)c(Cl)c3)CC2)cc1] |
| 21 | 1-(3,4-dichlorophenyl)-4-[(E)-2-[3-(trifluoromethyl)phenyl]diazen-1-yl]piperazine | 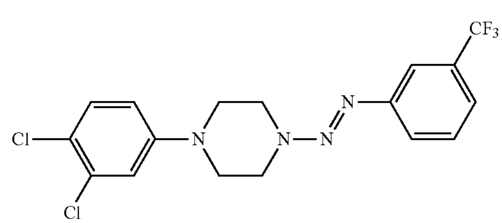 [SMILES: FC(F)(F)c1cccc(/N=N/N2CCN(c3ccc(Cl)c(Cl)c3)CC2)c1] |

TABLE 1-continued

| | Chemical name | Structure |
|---|---|---|
| 22 | 1-{4[(E)-2-[4-(3,4-dichlorophenyl)piperazin-1-yl]phenyl}ethan-1-one | 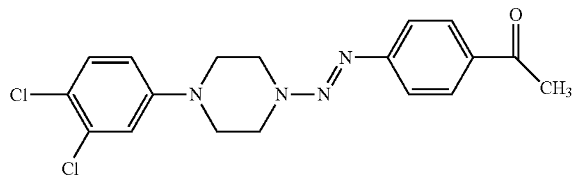 [SMILES: CC(=O)c1ccc(/N=N/N2CCN(c3ccc(Cl)c(Cl)c3)CC2)cc1] |
| 23 | 1-(2-methylphenyl)-4-[(E)-2-(4-nitrophenyl)diazen-1-yl]piperazine | 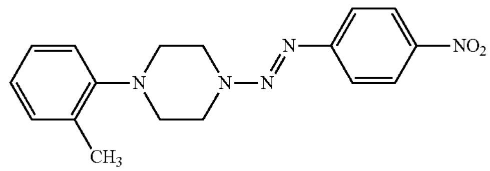 [SMILES: Cc1ccccc1N1CCN(/N=N/c2ccc([N+](=O)[O-])cc2)CC1] |
| 24 | 4-[(E)-2-[4-(2-methylphenyl)piperazin-1-yl]diazen-1-yl]benzamide | 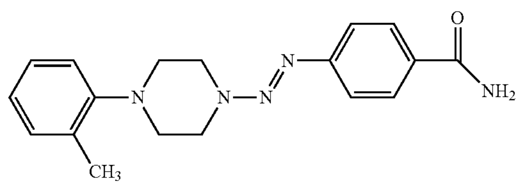 [SMILES: Cc1ccccc1N1CCN(/N=N/c2ccc(C(N)=O)cc2)CC1] |
| 25 | ethyl 4-[(E)-2-[2-methylphenyl)piperazin-1-yl]diazen-1-yl]benzoate | 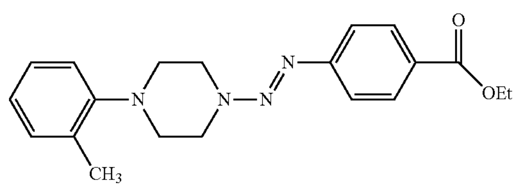 [SMILES: CCOC(=O)c1ccc(/N=N/N2CCN(c3ccccc3C)CC2)cc1] |
| 26 | 1-[(E)-2-(4-chlorophenyl)diazen-1-yl]-4-(2-methylphenyl)piperazine | 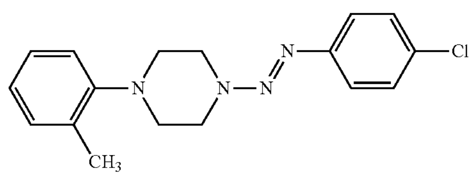 [SMILES: Cc1ccccc1N1CCN(/N=N/c2ccc(Cl)cc2)CC1] |
| 27 | 1-[(E)-2-(4-methoxyphenyl)diazen-1-yl]-4-(2-methylphenyl)piperazine | 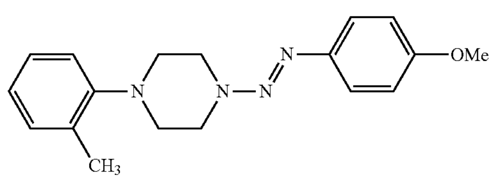 |
| 28 | 1-(2-methylphenyl)-4-[(E)-2-phenyldiazen-1-yl]piperazine | 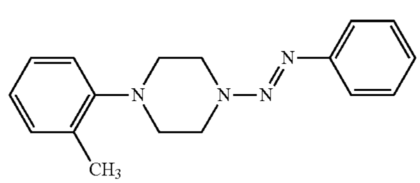 [SMILES: Cc1ccccc1N1CCN(/N=N/c2ccccc2)CC1] |
| 29 | 1-{4-[(E)-(2-methylphenyl)piperazin-1-yl]diazen-1-yl]phenyl}ethan-1-one | 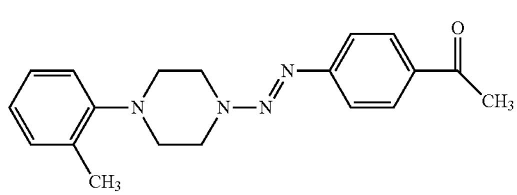 [SMILES: CC(=O)c1ccc(/N=N/N2CCN(c3ccccc3C)CC2)cc1] |

TABLE 1-continued

| | Chemical name | Structure |
|---|---|---|
| 30 | 1-[(E)-2-(4-bromophenyl)diazen-1-yl]-4-(4-fluorophenyl)piperazine | 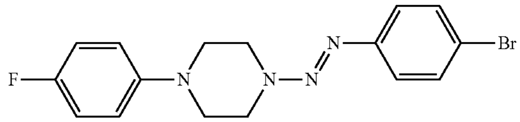 [SMILES: Fc1ccc(N2CCN(/N=N/c3ccc(Br)cc3)CC2)cc1] |
| 31 | 1-(4-fluorophenyl)-4-[(E)-2-(4-methylphenyl)diazen-1-yl]piperazine | 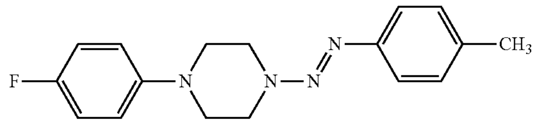 [SMILES: Cc1ccc(/N=N/N2CCN(c3ccc(F)cc3)CC2)cc1] |
| 32 | methyl 4-[(E)-2-[4[(4-fluorophenyl)piperazin-1-yl]diazen-1-yl]benzoate | 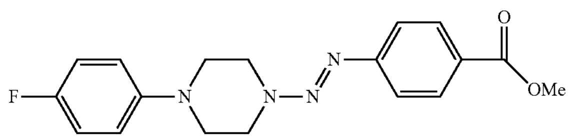 [SMILES: COC(=O)c1ccc(/N=N/N2CCN(c3ccc(F)cc3)CC2)cc1] |
| 33 | 1-(4-{4-[(E)-2-(4-bromophenyl)diazen-1-yl)piperazin-1-yl}phenyl)ethan-1-one | 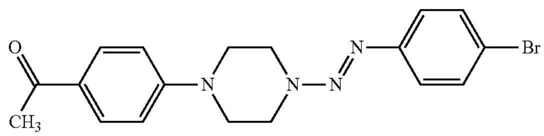 |
| 34 | 1-(4-{4-[(E)-2-(4-methylphenyl)diazen-1-yl)piperazin-1-yl}phenyl)ethan-1-one | 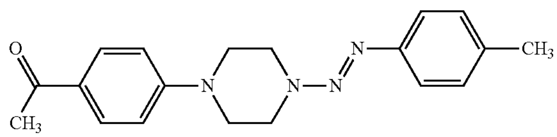 |
| 35 | methyl 4-[(E)-2-[4-(4-acetylphenyl)piperazin-1-yl]diazen-1-yl]benzoate | 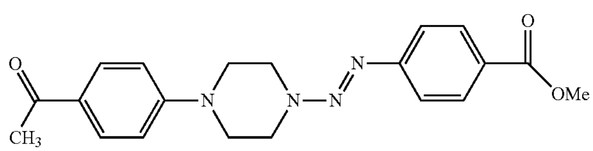 |
| 36 | 1-(4-{4-[(E)-2-(4-nitrophenyl)diazen-1-yl)piperazin-1-yl}phenyl)ethan-1-one | 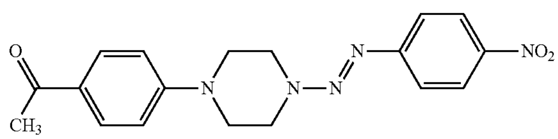 |
| 37 | 4-[(E)-2-[4-(4-acetylphenyl)piperazin-1-yl]diazen-1-yl]benzonitrile | 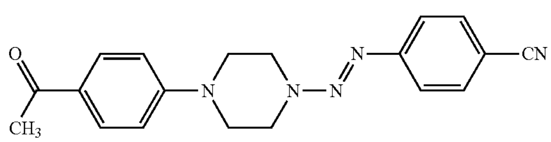 |
| 38 | ethyl 4-[(E)-2-[4-(4-acetylphenyl)piperazin-1-yl]diazen-1-yl]benzoate | 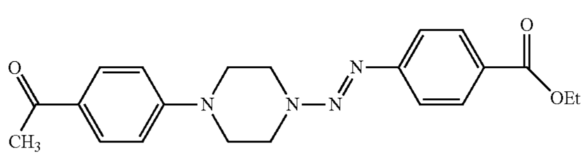 [SMILES: CCOC(=O)c1ccc(/N=N/N2CCN(c3ccc(C(C)=O)cc3)CC2)cc1] |
| 39 | 1-(4-{4-[(E)-2-phenyldiazen-1-yl]piperazin-1-yl}phenyl)ethan-1-one | 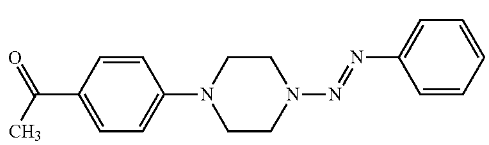 [SMILES: CC(=O)c1ccc(N2CCN(/N=N/c3ccccc3)CC2)cc1] |
| 40 | 1-[(E)-2-(4-nitrophenyl)diazen-1-yl]-4-(pyridine-2-yl)piperazine | 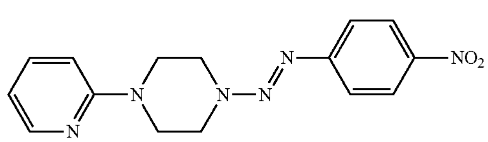 [SMILES: O=[N+]([O-])c1ccc(/N=N/N2CCN(c3ccccn3)CC2)cc1] |

TABLE 1-continued

| | Chemical name | Structure |
|---|---|---|
| 41 | 4-1(E)-2-[pyridin-2-yl)piperazin-1-yl]diazen-1-yl]benzonitrile | 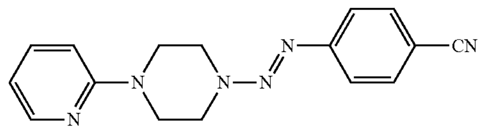 [SMILES: N#Cc1ccc(/N=N/N2CCN(c3ccccn3)CC2)cc1] |
| 42 | methyl 4-[(E)-2-[4-(pyridin-2-yl)piperazin-1-yl]diazen-1-yl]benzoate | 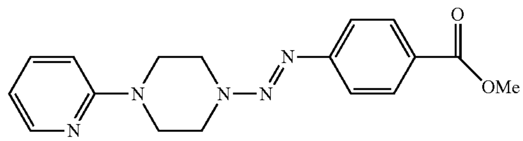 [SMILES: COC(=O)c1ccc(/N=N/N2CCN(c3ccccn3)CC2)cc1] |
| 43 | 1-[(E)-2-(4-bromophenyl)diazen-1-yl]-4-(pyridin-2-yl)piperazine | 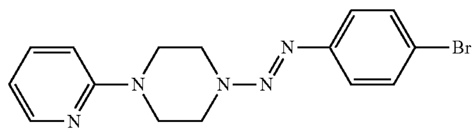 |
| 44 | 1-[(E)-2-(4-methylphenyl)diazen-1-yl]-4-(pyridin-2-yl)piperazine | 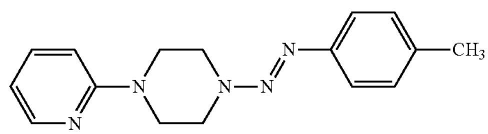 |
| 45 | 1-{2-[(E)-4-[pyridine-2-yl)piperazine-1-yl]diazen-1-yl]phenyl}ethan-1-one | 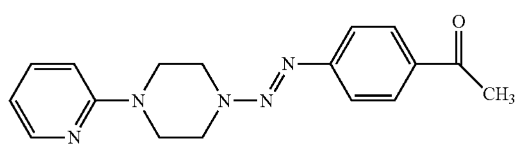 [SMILES: CC(=O)c1ccc(/N=N/N2CCN(c3ccccn3)CC2)cc1] |
| 46 | 1-[(E)-2-(2-bromophenyl)diazen-1-yl]-4-(pyridin-2-yl)piperazine | 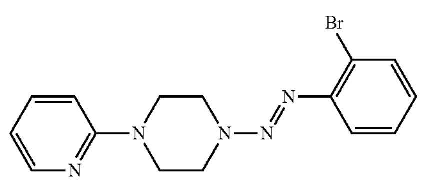 [SMILES: Brc1ccccc1/N=N/N1CCN(c2ccccn2)CC1] |
| 47 | 1-[(E)-2-(3-pyridyl)diazen-1-yl]-4-(pyridin-2-yl)piperazine | 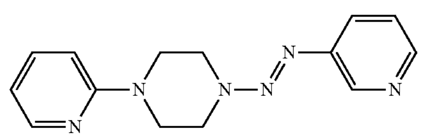 [SMILES: c1ccc(N2CCN(/N=N/c3cccnc3)CC2)nc1] |
| 48 | 1-[(E)-2-phenyldiazen-1-yl]-4-(pyridin-2-yl)piperazine | 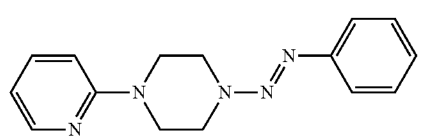 [SMILES: c1ccc(/N=N/N2CCN(c3ccccn3)CC2)cc1] |
| 49 | 2-{4-[(E)-2-(4-bromophenyl)diazen-1-yl]piperazin-1-yl}benzonitrile | 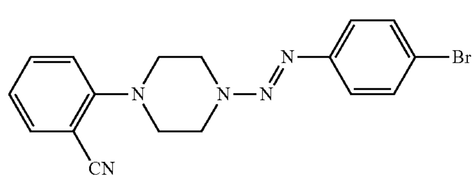 [SMILES: N#Cc1ccccc1N1CCN(/N=N/c2ccc(Br)cc2)CC1] |
| 50 | 2-{4-[(E)-2-(4-methylphenyl)diazen-1-yl]piperazin-1-yl}benzonitrile | 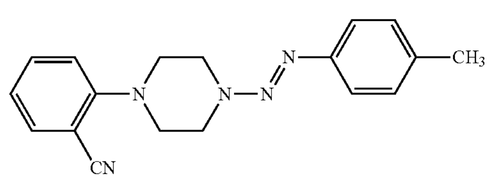 [SMILES: Cc1ccc(/N=N/N2CCN(c3ccccc3C#N)CC2)cc1] |

TABLE 1-continued

| | Chemical name | Structure |
|---|---|---|
| 51 | methyl 4-[(E)-2-[4-(2-cyanophenyl)piperazin-1-yl]diazen-1-yl]benzoate | 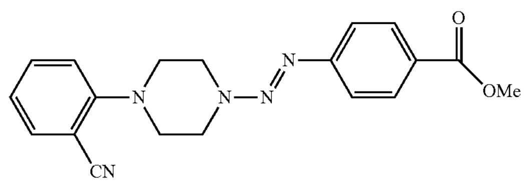 [SMILES: COC(=O)c1ccc(/N=N/N2CCN(c3ccccc3C#N)CC2)cc1] |
| 52 | 2-{4-[(E)-2-(4-methoxyphenyl)diazen-1-yl]piperazin-1-yl}benzonitrile | 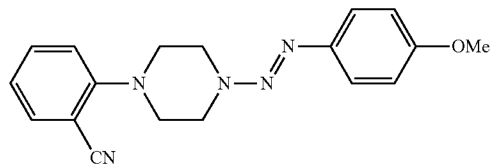 [SMILES: COc1ccc(/N=N/N2CCN(c3ccccc3C#N)CC2)cc1] |
| 53 | 1-(2,3-dimethylphenyl)-4-[(E)-2-(4-nitrophenyl)diazen-1-yl]piperazine | 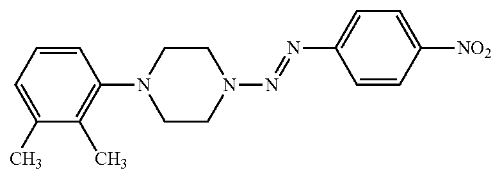 [SMILES: Cc1cccc(N2CCN(/N=N/c3ccc([N+](=O)[O-])cc3)CC2)c1C] |
| 54 | 4-[(E)-2-[4-(2,3-dimethylphenyl)piperazin-1-yl]diazen-1-yl]benzonitrile | 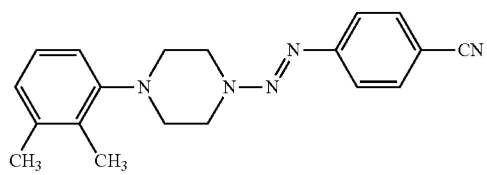 [SMILES: Cc1cccc(N2CCN(/N=N/c3ccc(C#N)cc3)CC2)c1C] |
| 55 | methyl 4-[(E)-2-[4-(2,3-dimethylphenyl)piperazin-1-yl]diazen-1-yl]benzoate | 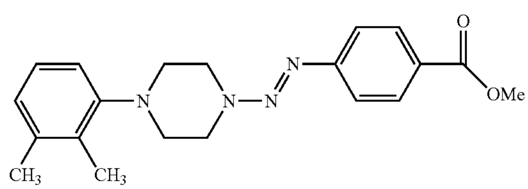 [SMILES: COC(=O)c1ccc(/N=N/N2CCN(c3cccc(C)c3C)CC2)cc1] |
| 56 | 1-[(E)-2-(4-bromophenyl)diazen-1-yl]-4-(2,3-dimethylphenyl)piperazine | 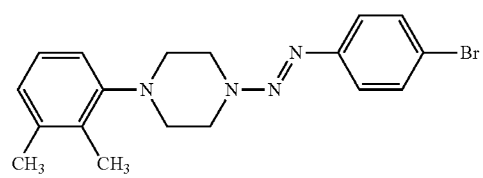 [SMILES: Cc1cccc(N2CCN(/N=N/c3ccc(Br)cc3)CC2)c1C] |
| 57 | 1-(2,3-dimethylphenyl)-4-[(E)-2-(4-methylphenyl)diazen-1-yl]piperazine | 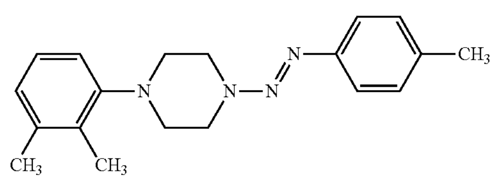 |
| 58 | 1-(2,3-dimethylphenyl)-4-[(E)-2-phenyldiazen-1-yl]piperazine | 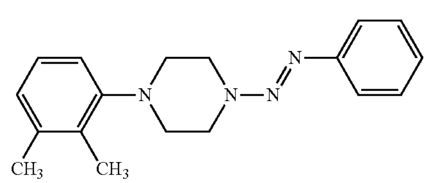 [SMILES: Cc1cccc(N2CCN(/N=N/c3ccccc3)CC2)c1C] |

TABLE 1-continued

| | Chemical name | Structure |
|---|---|---|
| 59 | 1-[(E)-2-(4-chlorophenyl)diazen-1-yl]-4-(2,3-dimethylphenyl)piperazine | 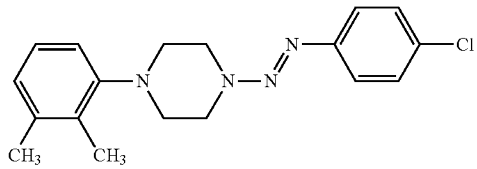 [SMILES: Cc1cccc(N2CCN(/N=N/c3ccc(Cl)cc3)CC2)c1C] |
| 60 | 1-(2,3-dimethylphenyl)-4-[(E)-2-(4-methoxyphenyl)diazen-1-yl]piperazine | 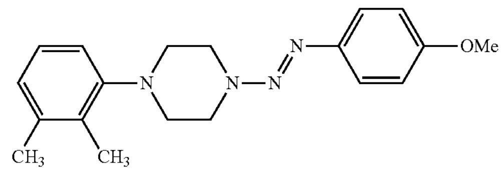 [SMILES: COc1ccc(/N=N/N2CCN(c3cccc(C)c3C)CC2)cc1] |
| 61 | 1-[(4-methylphenyl)methyl]-4-[(E)-2-(4-nitrophenyl)diazen-1-yl]piperazine | 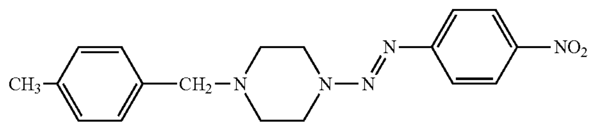 [SMILES: Cc1ccc(CN2CCN(/N=N/c3ccc([N+](=O)[O-])cc3)CC2)cc1] |
| 62 | 4-[(E)-2-{4-[(4-methylphenyl)methyl]piperazin-1-yl}diazen-1-yl]benzonitrile | 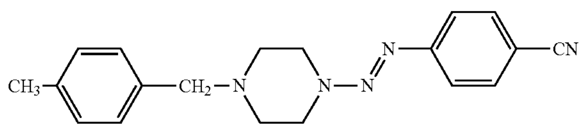 [SMILES: Cc1ccc(CN2CCN(/N=N/c3ccc(C#N)cc3)CC2)cc1] |
| 63 | methyl 4-[(E)-2-(4-[(4-methylphenyl)methyl]piperazin-1-yl}diazen-1-yl]benzoate | 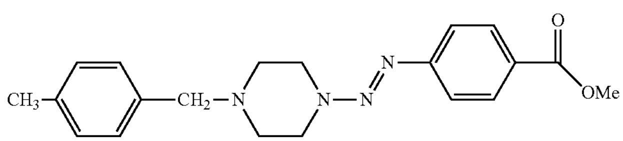 [SMILES: COC(=O)c1ccc(/N=N/N2CCN(Cc3ccc(C)cc3)CC2)cc1] |
| 64 | 1-[(E)-2-(4-bromophenyl)diazen-1-yl]-4-[(4-methylphenyl)methyl]piperazine | 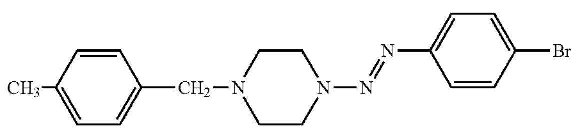 [SMILES: Cc1ccc(CN2CCN(/N=N/c3ccc(Br)cc3)CC2)cc1] |
| 65 | 1-[(E)-2-(4-methylphenyl)diazen-1-yl]-4-[(4-methylphenyl)rnethyl]piperazine | 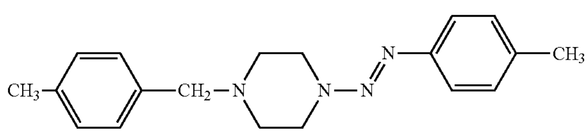 |
| 66 | 1-[(4-methylphenyl)methyl]-4-[(E)-2-phenyldiazen-1-yl]piperazine | 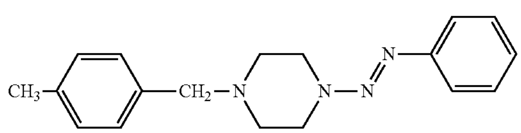 [SMILES: Cc1ccc(CN2CCN(/N=N/c3ccccc3)CC2)cc1] |
| 67 | 1-[(3-methylphenyl)methyl]-4-[(E)-2-(4-nitrophenyl)diazen-1-yl]piperazine | 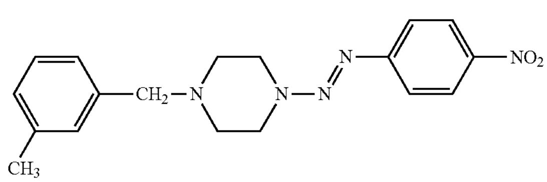 [SMILES: Cc1cccc(CN2CCN(/N=N/c3ccc([N+](=O)[O-])cc3)CC2)c1] |
| 68 | 4-[(E)-2-{4-[(3-methylphenyl)methyl]piperazin-1-yl}diazen-1-yl]benzonitrile | 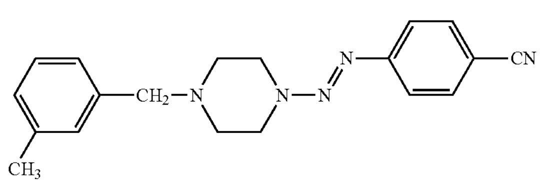 |

TABLE 1-continued

| | Chemical name | Structure |
|---|---|---|
| 69 | methyl 4-[(E)-2-{4-[(3-methylphenyl)methyl]piperazin-1-yl}diazen-1-yl]benzoate | 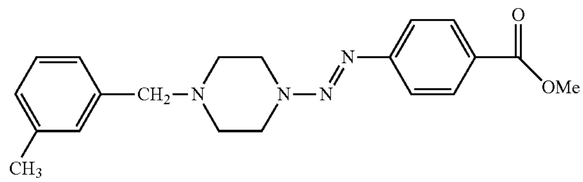 [SMILES: COC(=O)c1ccc(/N=N/N2CCN(Cc3cccc(C)c3)CC2)cc1] |
| 70 | 1-[(E)-2-(4-bromophenyl)diazen-1-yl]-4-[(3-methylphenyl)methyl]piperazine | 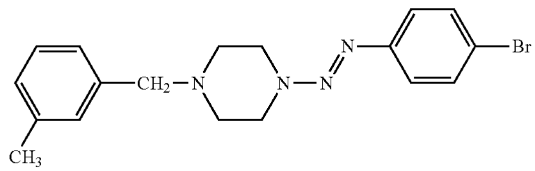 |
| 71 | 1-[(E)-2-(4-methylphenyl)diazen-1-yl]-4-[(3-methylphenyl)methyl]piperazine | 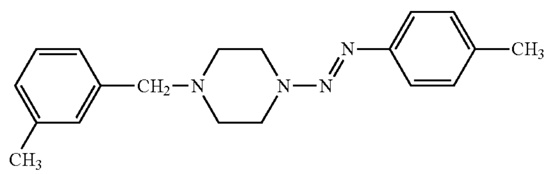 [SMILES: Cc1ccc(/N=N/N2CCN(Cc3cccc(C)c3)CC2)cc1] |
| 72 | 1-[(2-methylphenyl)methyl]-4-[(E)-2-(4-nitrophenyl)diazen-1-yl]piperazine | 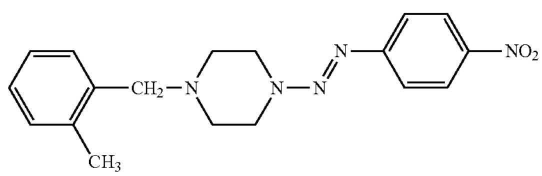 [SMILES: Cc1ccccc1CN1CCN(/N=N/c2ccc([N+](=O)[O-])cc2)CC1] |
| 73 | 4-[(E)-2-{4-[(2-methylphenyl)methyl]piperazin-1-yl}diazen-1-yl]benzonitrile | 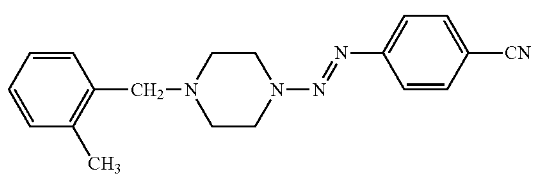 [SMILES: Cc1ccccc1CN1CCN(/N=N/c2ccc(C#N)cc2)CC1] |
| 74 | methyl 4-[(E)-2-{4-[(2-methylphenyl)methyl]piperazin-1-yl}diazen-1-yl]benzoate | 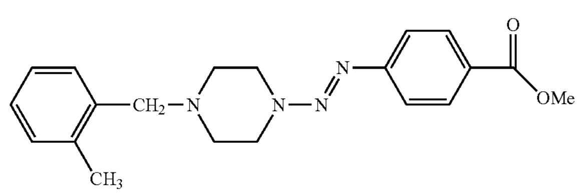 [SMILES: COC(=O)c1ccc(/N=N/N2CCN(Cc3ccccc3C)CC2)cc1] |
| 75 | 1-[(E)-2-(4-bromophenyl)diazen-1-yl]-4-[(2-methylphenyl)methyl]piperazine | 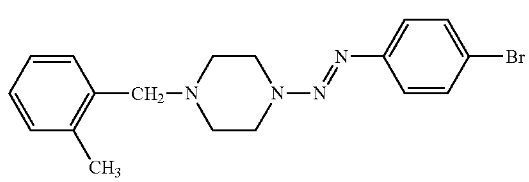 [SMILES: Cc1ccccc1CN1CCN(/N=N/c2ccc(Br)cc2)CC1] |
| 76 | 1-[(E)-2-(4-methylphenyl)diazen-1-yl]-4-[(2-methylphenyl)methyl]piperazine | 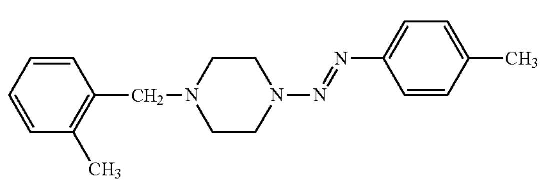 |

TABLE 1-continued

| | Chemical name | Structure |
|---|---|---|
| 77 | 1-[(2-methylphenyl)methyl]-4-[(E)-2-phenyldiazen-1-yl]-4-piperazine | 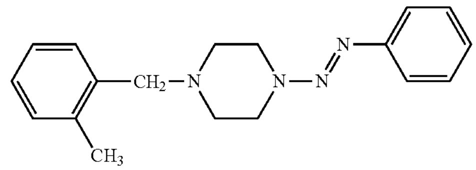 [SMILES: Cc1ccccc1CN1CCN(/N=N/c2ccccc2)CC1] |
| 78 | methyl 4-[(E)-2-[4-(2-phenylethyl)piperazin-1-yl]diazen-1-yl]benzoate | 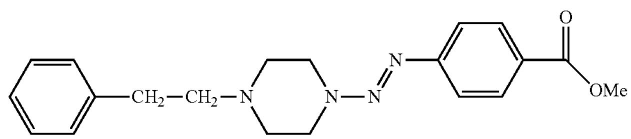 [SMILES: COC(=O)c1ccc(/N=N/N2CCN(CCc3ccccc3)CC2)cc1] |

The compounds of the present invention can be used or formulated for treatment of various cancers in mammals, including humans. In such cases, it may be advantageous or necessary to formulate the compound as a pharmaceutically acceptable salt. Examples of cancers in which the compounds may have efficacy include breast, brain, in particular glioblastomas, lung, and colon.

The chemical compound of the invention may be provided in any form suitable for the intended administration. Suitable forms include pharmaceutically (i.e. physiologically) acceptable salts, and pre- or prodrug forms of the chemical compound on the invention.

Examples of pharmaceutically acceptable addition salts include, without limitation, the non-toxic inorganic and organic acid addition salts such as the hydrochloride derived from hydrocholoric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconitate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enanthate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphthalene-2-sulphonic acid, the phthalate derived from phthalic acid, the salicylate derived from salicyclic acid, the sorbate derived from sorbic acid, the stearate derived from stearic acid, the succinate derived from succinic acid, the tartrate derived from tartartic acid, the toluene-p-sulphonate derived from p-toluene-sulphonic acid, and the like. Such salts may be formed by procedures well known and described in the art.

Other acids, such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

In the context of this invention the "onium salts" of N- and/or S-containing compounds are also contemplated as pharmaceutically acceptable salts. Preferred "onium salts" include the alkyl-onium salts, the cycloalkyl-onium salts, and the cycloalkylalkyl-onium salts.

The compound of the invention may be provided in dissoluble or indissoluble forms together with a pharmaceutically acceptable solvent, such as water, ethanol, and the like. Dissoluble forms may also include hydrated forms, such as the monohydrate, the dehydrate, the hemihydrate, the trihydrate, the tetrahydrate, and the like. In general, the dissoluble forms are considered equivalent to indissoluble forms for the purposes of this invention.

The compounds of the present invention can be formulated into a pharmaceutical composition in combination with a pharmaceutically acceptable carrier.

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semi-permeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals.

The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

EXAMPLES

Example 1

Synthesis of N-aryl-N-aryldiazenylpiperazines

All reagents were reagent grade materials purchased from Sigma-Aldrich Canada Ltd. and were used without further purification. The aromatic primary ($ArNH_2$) amine (0.010 mole) was dissolved in 3M aqueous hydrochloric acid (12.0 mL), and placed in an ice bath to cool to 0° C. A solution of sodium nitrite (0.011 mole) in water (3.0 mL) was added to the solution, and the mixture stirred for 0.5 hours in the cold to give the diazonium salt. Concurrently, the appropriate piperazine derivative (0.010 mole) was dissolved in water (10.0 mL), and cooled to 0° C. The piperazine solution was added slowly to the diazonium salt solution, and the resulting mixture was stirred for 0.5 hours in the cold. The solution was then neutralized with saturated sodium bicarbonate and left stirring in the cold for two hours. The product was collected using vacuum filtration if it was a solid and by extraction with dichloromethane if it was an oil. The solids were purified by recrystallization using an appropriate solvent. Products were characterized as follows:

Melting points were determined on a Fisher-Johns or Electrothermal Mel-Temp melting point apparatus, and are uncorrected.

Infrared spectra were obtained by neat methods or by using Nujol mulls on a Bruker Vector 22 spectrometer.

$^1$H NMR spectra were obtained with either the Bruker AC250 MHz or AV500 MHz spectrometers at the Atlantic Regional Magnetic Resonance Center at Dalhousie University. Chemical shifts were recorded in $CDCl_3$ or d6-DMSO at 27° C., and are relative to TMS as the internal standard.

Mass spectrometry: Accurate mass measurements were made on a CEC 21-110B mass spectrometer operated at a mass resolution of 8000 (10% valley) by computer controlled peak matching to appropriate PFK reference ions. Spectra were obtained using electron ionization at 70 volts and a source temperature of 170° C., with samples being introduced by means of a heatable quartz probe. The standard deviation of mass measurement is +/−0.0008 amu, which is an average of 3.6 ppm over the mass range 100 to 300 amu.

Examples of compounds synthesized by this method are shown in Table 1 as compounds 1-9.

Example 2

Synthesis of N-aryl-N-aryldiazenylpiperzines-chloro derivatives

These compounds were synthesized according to the method described in Example 1.

Examples of these compounds are shown in Table 1 as compounds 10-15.

Example 3

Synthesis of N-aryl-N-aryldiazenylpiperzines-dichloro derivatives

These compounds were synthesized according to the method described in Example 1.

Examples of these compounds are shown in Table 1 as compounds 16-22.

Example 4

Synthesis of N-aryl-N-aryldiazenylpiperzines-o-methyl derivatives

These compounds were synthesized according to the method described in Example 1.

Examples of these compounds are shown in Table 1 as compounds 23-29.

Example 5

Synthesis of N-aryl-N-aryldiazenylpiperzines-p-floro derivatives

These compounds were synthesized according to the method described in Example 1.

Examples of these compounds are shown in Table 1 as compounds 30-32.

Example 6

Synthesis of N-aryl-N-aryldiazenylpiperzines-p-acetyl derivatives

These compounds were synthesized according to the method described in Example 1.

Examples of these compounds are shown in Table 1 as compounds 33-39.

Example 7

Synthesis of N-aryl-N-aryldiazenylpiperzines-2-pyridyl derivatives

These compounds were synthesized according to the method described in Example 1.

Examples of these compounds are shown in Table 1 as compounds 40-48.

Example 8

Synthesis of N-aryl-N-aryldiazenylpiperzines-cyano derivatives

These compounds were synthesized according to the method described in Example 1.

Examples of these compounds are shown in Table 1 as compounds 49-52.

Example 9

Synthesis of N-aryl-N-aryldiazenylpiperzines-dimethyl derivatives

All reagents were reagent grade materials purchased from Sigma-Aldrich Canada Ltd. and were used without further purification. The aromatic primary ($ArNH_2$) amine (0.006 mole) was dissolved in 3M aqueous hydrochloric acid (6.0 mL), and placed in an ice bath to cool to 0° C. A solution of sodium nitrite (0.006 mole) in water (3.0 mL) was added to the solution, and the mixture stirred for 0.5 hours in the cold to give the diazonium salt. Concurrently, the appropriate piperazine derivative (0.006 mole) was dissolved in water (10.0 mL), and cooled to 0° C. The piperazine solution was added slowly to the diazonium salt solution, and the resulting mixture was stirred for 0.5 hours in the cold. The solution was then neutralized with saturated sodium bicarbonate and left stirring in the cold for two hours. The product was collected using vacuum filtration if it was a solid and by extraction with dichloromethane if it was an oil. The solids were purified by recrystallization using an appropriate solvent. Products were characterized as follows:

Melting points were determined on a Fisher-Johns or Electrothermal Mel-Temp melting point apparatus, and are uncorrected.

Infrared spectra were obtained by neat methods or by using Nujol mulls on a Bruker Vector 22 spectrometer.

$^1$H NMR spectra were obtained with either the Bruker AC250 MHz or AV500 MHz spectrometers at the Atlantic Regional Magnetic Resonance Center at Dalhousie University. Chemical shifts were recorded in $CDCl_3$ or d6-DMSO at 27° C., and are relative to TMS as the internal standard.

Mass spectrometry: Accurate mass measurements were made on a CEC 21-110B mass spectrometer operated at a mass resolution of 8000 (10% valley) by computer controlled peak matching to appropriate PFK reference ions. Spectra were obtained using electron ionization at 70 volts and a source temperature of 170° C., with samples being introduced by means of a heatable quartz probe. The standard deviation of mass measurement is +/−0.0008 amu, which is an average of 3.6 ppm over the mass range 100 to 300 amu.

Examples of these compounds are shown in Table 1 as compounds 53-60.

Example 10

Synthesis of N-aryl-N-aryldiazenylpiperzines-p-methyl-methylphenyl derivatives

These compounds were synthesized according to the method described in Example 9.

Examples of these compounds are shown in Table 1 as compounds 61-66.

Example 11

Synthesis of N-aryl-N-aryldiazenylpiperzines-m-methyl-methylphenyl derivatives

These compounds were synthesized according to the method described in Example 9.

Examples of these compounds are shown in Table 1 as compounds 67-71.

Example 12

Synthesis of N-aryl-N-aryldiazenylpiperzines-o-methyl-methylphenyl derivatives

These compounds were synthesized according to the method described in Example 9.

Examples of these compounds are shown in Table 1 as compounds 72-77.

Example 13

Synthesis of N-aryl-N-aryldiazenylpiperzines-dimethylphenyl derivatives

These compounds were synthesized according to the method described in Example 9.

Examples of these compounds are shown in Table 1 as compound 78.

Example 14

Cytotoxicity of Glioblastoma Cancer Cells

U87MG glioblastoma cancer cells were cultured according to established protocols (Martinkova et al., Cytotoxicity of and DNA adduct formation by ellipicine in human U87MG glioblastoma cancer cells. Neuro Endocrinol Lett 30 (Suppl 1):60-6, 2009). Temozolomide was added to the cell culture media at increasing doses and the relative cell density, as a percent of control cells not exposed to temozolomide, was calculated. Temozolomide is one of the primary treatments for glioblastoma type cancers and dacarbazine is an antineoplastic chemotherapy used in the treatment of various cells. As shown in FIG. 1, the LD50 of Temozolomide was calculated to be 25.54 µM and the LD50 of dacarbazine was 25.0 µM.

To test the cytotoxic effect of 1-[(E)-2-(4-nitrophenyl)diazen-1-yl]-4-phenylpiperazine, 4-[(E)-2-(4-phenylpiperazin-1-yl)diazen-1-yl]benzonitrile, methyl 4-[(E)-2-(4-phenylpiperazin-1-yl)diazen-1-yl]benzoate, methyl 4-[(E)-2-[4-(4-chlorophenyl)piperazin-1-yl)diazen-1-yl]benzoate, 1-[(E)-2-(4-bromophenyl)diazen-1-yl]-4-[(3-methylphenyl)methyl]piperazine, 4-[(E)-2-{4-[(3-methylphenyl)methyl]piperazin-1-yl}diazen-1-yl]benzonitrile serial dilutions of the compounds were made and added to the cell culture media containing the U87MG glioblastoma cancer cells. The relative cell density, as a percent of control cells not exposed to temozolomide, dacarbazine or the experimental compounds, was calculated. All six experimental compounds were shown to be more cytotoxic than temozolomide and. In particular, 1-[(E)-2-(4-nitrophenyl)diazen-1-yl]-4-phenylpiperazine had a LD50 of 4.361 µM. 4-[(E)-2-(4-phenylpiperazin-1-yl)diazen-1-yl]benzonitrile had a LD50 of 12.44 µM. Methyl 4-[(E)-2-(4-phenylpiperazin-1-yl)diazen-1-yl]benzoate had a LD50 of 16.17 µM. Methyl 4-[(E)-2-[4-(4-chlorophenyl)piperazin-1-yl)diazen-1-yl]benzoate, had a LD50 of 22.25 µM. 1-[(E)-2-(4-bromophenyl)diazen-1-yl]-4-[(3-methylphenyl)methyl]piperazine had a LD50 of 12.2 µM. 4-[(E)-2-{4-[(3-methylphenyl)methyl]piperazin-1-yl}diazen-1-yl]benzonitrile had a LD50 of 13.99 µM.

Example 15

Cytotoxicity of A549 Lung Cancer Cells

Figure 2:
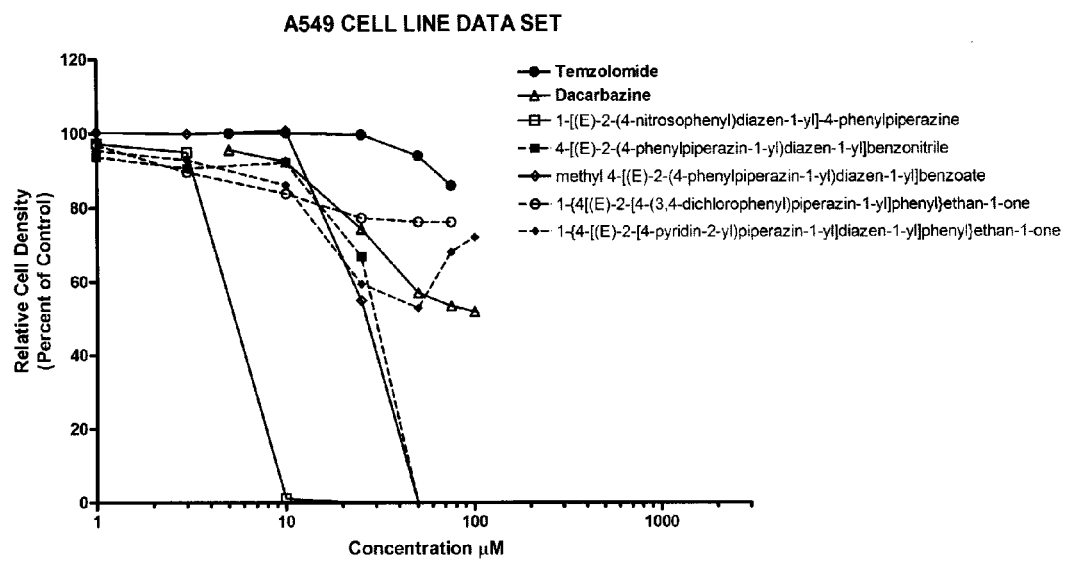
FIG. 2 is a graphical representation of the relative cell density of A549 lung cancer cells exposed to varying concentrations of temozolomide, dacarbazine, 1-[(E)-2-(4-nitrophenyl)diazen-1-yl]-4-phenylpiperazine, methyl 4-[(E)-2-(4-phenylpiperazin-1-yl)diazen-1-yl]benzoate, 1-{4[(E)-2-[4-(3,4-dichlorophenyl)piperazin-1-yl]phenyl}ethan-1-one and 1-{4-[(E)-2-[4-pyridin-2-yl)piperazin-1-yl]diazen-1-yl]phenyl}ethan-1-one.

A549 lung cancer cells were cultured according to established protocols (Lieber M. et al., Int. J. Cancer 17: 62-70, 1976). Temozolomide and dacarbazine were separately added to the cell culture media at increasing doses and the relative cell density, as a percent of control cells not exposed to temozolomide or dacarbazine, was calculated. As shown in FIG. 2, the LD50 of dacarbazine was calculated to be 25.7 µM, whereas the LD50 of temozolomide was 60.4 µM in this cell line.

To test the cytotoxic effect of 1-[(E)-2-(4-nitrophenyl)diazen-1-yl]-4-phenylpiperazine, methyl 4-[(E)-2-(4-phenylpiperazin-1-yl)diazen-1-yl]benzoate, 1-{4[(E)-2-[4-(3,4-dichlorophenyl)piperazin-1-yl]phenyl}ethan-1-one, 1-{4-[(E)-2-[4-pyridin-2-yl)piperazin-1-yl]diazen-1-yl]phenyl}ethan-1-one, serial dilutions of the compounds were made and added to the cell culture media containing the A549 lung cancer cells. The relative cell density, as a percent of control cells not exposed to temozolomide, dacarbazine or the experimental compounds, was calculated. All four experimental compounds were shown to be more cytotoxic than temozolomide and, more importantly, dacarbazine. In particular, 1-[(E)-2-(4-nitrophenyl)diazen-1-yl]-4-phenylpiperazine had a LD50 of 5.27 µM. Methyl 4-[(E)-2-(4-phenylpiperazin-1-yl)diazen-1-yl]benzoate had a LD50 of 25.5 µM. 1-{4[(E)-2-[4-(3,4-dichlorophenyl)piperazin-1-yl]phenyl}ethan-1-one had a LD50 of 3.4 µM. 1-{4-[(E)-2-[4-pyridin-2-yl)piperazin-1-yl]diazen-1-yl]phenyl}ethan-1-one had a LD50 of 15.6 µM.

Example 16

Cytotoxicity of HT29 Colon Cancer Cells

Figure 3:
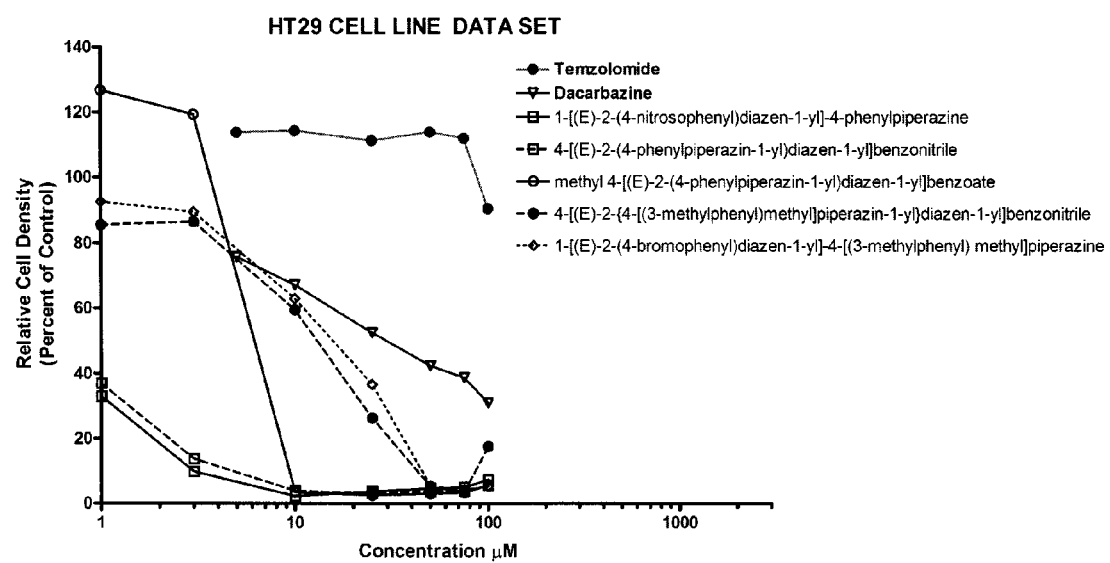
FIG. 3 is a graphical representation of the relative cell density of HT29 colon cancer cells exposed to varying concentrations of temozolomide, dacarbazine, 1-[(E)-2-(4-nitrophenyl)diazen-1-yl]-4-phenylpiperazine, 4-[(E)-2-(4-phenylpiperazin-1-yl)diazen-1-yl]benzonitrile, methyl 4-[(E)-2-(4-phenylpiperazin-1-yl)diazen-1-yl]benzoate, methyl 4-[(E)-2-[4-(4-chlorophenyl)piperazin-1-yl)diazen-1-yl]benzoate, 1-[(E)-2-(4-bromophenyl)diazen-1-yl]-4-[(3-methylphenyl)methyl]piperazine, and 4-[(E)-2-{4-[(3-methylphenyl)methyl]piperazin-1-yl}diazen-1-yl]benzonitrile.

HT29 colon cancer cells were cultured according to established protocols Mitchell, R B and Dolan, M E Cancer Chemother. Pharmacol. 32(1): 59-63, 1993). Dacarbazine was added to the cell culture media at increasing doses and the relative cell density, as a percent of control cells not exposed to dacarbazine, was calculated. As shown in FIG. 3, the LD50 of dacarbazine was calculated to be 25.2 µM.

To test the cytotoxic effect of 1-[(E)-2-(4-nitrophenyl)diazen-1-yl]-4-phenylpiperazine, 4-[(E)-2-(4-phenylpiperazin-1-yl)diazen-1-yl]benzonitrile, methyl 4-[(E)-2-(4-phenylpiperazin-1-yl)diazen-1-yl]benzoate, 1-[(E)-2-(4-methylphenyl)diazen-1-yl]-4-phenylpiperazine, 1-{4[(E)-2-[4-(3,4-dichlorophenyl)piperazin-1-yl]phenyl}ethan-1-one, methyl 4-[(E)-2-[4-(pyridin-2-yl)piperazin-1-yl]diazen-1-yl]benzoate, 1-{4-[(E)-2-[4-pyridin-2-yl)piperazin-1-yl]diazen-1-yl]phenyl}ethan-1-one, 2-{4-[(E)-2-(4-bromophenyl)diazen-1-yl]piperazin-1-yl}benzonitrile, 4-[(E)-2-{4-[(3-methylphenyl)methyl]piperazin-1-yl}diazen-1-yl]benzonitrile, 1-[(E)-2-(4-bromophenyl)diazen-1-yl]-4-[(3-methylphenyl)methyl]piperazine, serial dilutions of the compounds were made and added to the cell culture media containing the U87MG glioblastoma cancer cells. The relative cell density, as a percent of control cells not exposed to Temozolomide or the experimental compounds, was calculated. All ten experimental compounds were shown to be more cytotoxic than dacarbazine. In particular, 1-[(E)-2-(4-nitrophenyl)diazen-1-yl]-4-phenylpiperazine had a LD50 of 2.5 µM. 4-[(E)-2-(4-phenylpiperazin-1-yl)diazen-1-yl]benzonitrile had a LD50 of 2.6 µM. Methyl 4-[(E)-2-(4-phenylpiperazin-1-yl)diazen-1-yl]benzoate had a LD50 of 3.9 µM. 1-[(E)-2-(4-methylphenyl)diazen-1-yl]-4-phenylpiperazine had a LD50 of 9.6 µM. 1-{4[(E)-2-[4-(3,4-dichlorophenyl)piperazin-1-yl]phenyl}ethan-1-one had a LD50 of 3.4 µM. Methyl 4-[(E)-2-[4-(pyridin-2-yl)piperazin-1-yl]diazen-1-yl]benzoate had a LD50 of 14.6 µM. 1-{4-[(E)-2-[4-pyridin-2-yl)piperazin-1-yl]diazen-1-yl]phenyl}ethan-1-one had a LD50 of 11.2 µM. 2-{4-[(E)-2-(4-bromophenyl)diazen-1-yl]piperazin-1-yl}benzonitrile had a LD50 of 5.2 µM. 4-[(E)-2-{4-[(3-methylphenyl)methyl]piperazin-1-yl}diazen-1-yl]benzonitrile had a LD50 of 13.5 µM. 1-[(E)-2-(4-bromophenyl)diazen-1-yl]-4-[(3-methylphenyl)methyl]piperazine had a LD50 of 17.6 µM.

The invention claimed is:
1. A compound having the general formula (I):

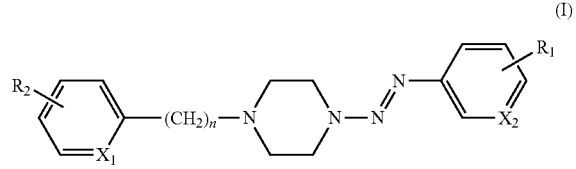

(I)

where
n is selected from the group consisting of 0, 1 and 2;
$X_1$ is CH, CCH$_3$, CC≡N, or N;
$X_2$ is CH or N;
R1 is absent or is selected from the group consisting of alkyl, halogen, ether, cyano, pyridyl, COCR$_3$, CO$_2$R$_4$, CONH$_2$, NO$_2$, and CF$_3$;
R2 is absent or represents one or more substituents selected from the group consisting of halogen, alkyl, pyridyl, cyano, acetyl, phenyl and phenyl substituted with alkyl;
R3 is selected from the group consisting of hydrogen, alkyl and CONH$_2$; and
R4 is alkyl,
wherein at least one of R1 or R2 is present.

2. The compound of claim 1, wherein R1 is selected from the group consisting of para-nitro, para-cyanide, para-chloride, para-bromide, para-methyl, ortho-bromide, para-methyl ether, meta-trifluoromethyl, hydrogen, para-ethyl ester, para-methyl ester, para-acetyl and 3-pyridyl.

3. The compound of claim 1, wherein R2 is absent or is selected from the group consisting of para-chloride, meta-, para-dichloride, ortho-methyl, para-fluoride, para-acetyl, 2-pyridyl, ortho-cyanide, and meta-, ortho-methyl.

4. The compound of claim 1, wherein:
n=1;
R1 is selected from the group consisting of para-nitro, para-cyanide, para-bromide, para-methyl, hydrogen, para-methyl ether and para-methyl ester; and
R2 is selected from the group consisting of para-methyl, ortho-methyl and meta-methyl.

5. The compound of claim 1, wherein:
n=2;
R1 is para-methyl ester; and
R2 is absent.

6. A compound selected from the group consisting of
1-[(E)-2-(4-nitrophenyl)diazen-1-yl]-4-phenylpiperazine;
4-[(E)-2-(4-phenylpiperazin-1-yl)diazen-1-yl]benzonitrile;
Methyl 4-[(E)-2-(4-phenylpiperazin-1-yl)diazen-1-yl]benzoate;
1-{4-[(E)-2-(4-phenylpiperazin-1-yl)diazen-1-yl]phenyl}ethan-1-one;
1-[(E)-2-(4-chlorophenyl)diazen-1-yl]-4-phenylpiperazine;
1-[(E)-2-(4-bromophenyl)diazen-1-yl]-4-phenylpiperazine;
1-[(E)-2-(4-methylphenyl)diazen-1-yl]-4-phenylpiperazine;
1-[(E)-2-(4-methoxyphenyl)diazen-1-yl]-4-phenylpiperazine;
1-[(E)-2-(2-bromophenyl)diazen-1-yl]-4-phenylpiperazine;
1-(4-chlorophenyl)-4-[(E)-2-(4-nitrophenyl)diazen-1-yl]piperazine;
4-[(E)-2-[4-(4-chlorophenyl)piperazin-1-yl]diazen-1-yl]benzonitrile;
methyl 4-[(E)-2-[4-(4-chlorophenyl)piperazin-1-yl)diazen-1-yl]benzoate;
1-[(E)-2-(4-bromophenyl)diazen-1-yl]-4-(4-chlorophenyl) piperazine;
1-(4-chlorophenyl)-4-[(E)-2-(4-methylphenyl)diazen-1-yl]piperazine;
1-(4-chlorophenyl)-4-[(E)-2-(4-methoxyphenyl)diazen-1-yl]piperazine;
1-(3,4-dichlorophenyl)-4-[(E)-2-(4-nitrophenyl)diazen-1-yl]piperazine;
4-[(E)-2-[4-(3,4-dichlorophenyl)piperazin-1-yl]diazen-1-yl]benzonitrile;
1-[(E)-2-(4-bromophenyl)diazen-1-yl]-4-(3,4-dichlorophenyl)piperazine;
1-(3,4-dichlorophenyl)-4-[(E)-2-(4-methylphenyl)diazen-1-yl]piperazine;
1-(3,4-dichlorophenyl)-4-[(E)-2-(4-methoxyphenyl)diazen-1-yl]piperazine;
1-(3,4-dichlorophenyl)-4-[(E)-2-[3-(trifluoromethyl)phenyl]diazen-1-yl]piperazine;
1-{4[(E)-2-[4-(3,4-dichlorophenyl)piperazin-1-yl]phenyl}ethan-1-one;
1-(2-methylphenyl)-4-[(E)-2-(4-nitrophenyl)diazen-1-yl]piperazine;
4-[(E)-2-[4-(2-methylphenyl)piperazin-1-yl]diazen-1-yl]benzamide;
ethyl 4-[(E)-2-[4-methylphenyl)piperazin-1-yl]diazen-1-yl]benzoate;
1-[(E)-2-(4-chlorophenyl)diazen-1-yl]-4-(2-methylphenyl)piperazine;
1-[(E)-2-(4-methoxyphenyl)diazen-1-yl]-4-(2-methylphenyl)piperazine;
1-(2-methylphenyl)-4-[(E)-2-phenyldiazen-1-yl]piperazine;
1-{4-[(E)-(2-methylphenyl)piperazin-1-yl]diazen-1-yl]phenyl}ethan-1-one;
1-[(E)-2-(4-bromophenyl)diazen-1-yl]-4-(4-fluorophenyl) piperazine;
1-(4-fluorophenyl)-4-[(E)-2-(4-methylphenyl)diazen-1-yl]piperazine;
methyl 4-[(E)-2-[4[(4-fluorophenyl)piperazin-1-yl]diazen-1-yl]benzoate;
1-(4-{4-[(E)-2-(4-bromophenyl)diazen-1-yl)piperazin-1-yl}phenyl)ethan-1-one;
1-(4-{4-[(E)-2-(4-methylphenyl)diazen-1-yl)piperazin-1-yl}phenyl)ethan-1-one;
methyl 4-[(E)-2-[4-(4-acetylphenyl)piperazin-1-yl]diazen-1-yl]benzoate;
1-(4-{4-[(E)-2-(4-nitrophenyl)diazen-1-yl)piperazin-1-yl}phenyl)ethan-1-one;
4-[(E)-2-[4-(4-acetylphenyl)piperazin-1-yl]diazen-1-yl] benzonitrile;
ethyl 4-[(E)-2-[4-(4-acetylphenyl)piperazin-1-yl]diazen-1-yl]benzoate;
1-(4-{4-[(E)-2-phenyldiazen-1-yl]piperazin-1-yl}phenyl)ethan-1-one;
1-[(E)-2-(4-nitrophenyl)diazen-1-yl]-4-(pyridine-2-yl) piperazine;
4-[(E)-2-[pyridin-2-yl)piperazin-1-yl]diazen-1-yl]benzonitrile;
methyl 4-[(E)-2-[4-(pyridin-2-yl)piperazin-1-yl]diazen-1-yl]benzoate;
1-[(E)-2-(4-bromophenyl)diazen-1-yl]-4-(pyridin-2-yl) piperazine;
1-[(E)-2-(4-methylphenyl)diazen-1-yl]-4-(pyridin-2-yl) piperazine;
1-{2-[(E)-4-[pyridine-2-yl)piperazine-1-yl]diazen-1-yl]phenyl}ethan-1-one;
1-[(E)-2-(2-bromophenyl)diazen-1-yl]-4-(pyridin-2-yl) piperazine;
1-[(E)-2-(3-pyridyl)diazen-1-yl]-4-(pyridin-2-yl)piperazine;
1-[(E)-2-phenyldiazen-1-yl]-4-(pyridin-2-yl)piperazine;
2-{4-[(E)-2-(4-bromophenyl)diazen-1-yl]piperazin-1-yl}benzonitrile;
2-{4-[(E)-2-(4-methylphenyl)diazen-1-yl]piperazin-1-yl}benzonitrile;
methyl 4-[(E)-2-[4-(2-cyanophenyl)piperazin-1-yl]diazen-1-yl]benzoate;

2-{4-[(E)-2-(4-methoxyphenyl)diazen-1-yl]piperazin-1-yl}benzonitrile;
1-(2,3-dimethylphenyl)-4-[(E)-2-(4-nitrophenyl)diazen-1-yl]piperazine
4-[(E)-2-[4-(2,3-dimethylphenyl)piperazin-1-yl]diazen-1-yl]benzonitrile;
methyl 4-[(E)-2-[4-(2,3-dimethylphenyl) piperazin-1-yl]diazen-1-yl]benzoate;
1-[(E)-2-(4-bromophenyl)diazen-1-yl]-4-(2,3-dimethylphenyl) piperazine;
1-(2,3-dimethylphenyl)-4-[(E)-2-(4-methylphenyl)diazen-1-yl]piperazine;
1-(2,3-dimethylphenyl)-4-[(E)-2-phenyldiazen-1-yl]piperazine;
1-[(E)-2-(4-chlorophenyl)diazen-1-yl]-4-(2,3-dimethylphenyl) piperazine;
1-(2,3-dimethylphenyl)-4-[(E)-2-(4-methoxyphenyl)diazen-1-yl]piperazine;
1-[(4-methylphenyl)methyl]-4-[(E)-2-(4-nitrophenyl)diazen-1-yl]piperazine;
4-[(E)-2-{4-[(4-methylphenyl)methyl]piperazin-1-yl}diazen-1-yl]benzonitrile;
methyl 4-[(E)-2-{4-[(4-methylphenyl)methyl]piperazin-1-yl}diazen-1-yl]benzoate;
1-[(E)-2-(4-bromophenyl)diazen-1-yl]-4-[(4-methylphenyl)methyl]piperazine;
1-[(E)-2-(4-methylphenyl)diazen-1-yl]-4-[(4-methylphenyl)methyl]piperazine;
1-[(4-methylphenyl)methyl]-4-[(E)-2-phenyldiazen-1-yl] piperazine;
1-[(3-methylphenyl)methyl]-4-[(E)-2-(4-nitrophenyl)diazen-1-yl]piperazine;
4-[(E)-2-{4-[(3-methylphenyl)methyl]piperazin-1-yl}diazen-1-yl]benzonitrile;
methyl 4-[(E)-2-{4-[(3-methylphenyl)methyl]piperazin-1-yl}diazen-1-yl]benzoate;
1-[(E)-2-(4-bromophenyl)diazen-1-yl]-4-[(3-methylphenyl)methyl]piperazine;
1-[(E)-2-(4-methylphenyl)diazen-1-yl]-4-[(3-methylphenyl)methyl]piperazine;
1-[(2-methylphenyl)methyl]-4-[(E)-2-(4-nitrophenyl)diazen-1-yl]piperazine;
4-[(E)-2-{4-[(2-methylphenyl)methyl]piperazin-1-yl}diazen-1-yl]benzonitrile;
methyl 4-[(E)-2-{4-[(2-methylphenyl)methyl]piperazin-1-yl}diazen-1-yl]benzoate;
1-[(E)-2-(4-bromophenyl)diazen-1-yl]-4[(2-methylphenyl)methyl]piperazine;
1-[(E)-2-(4-methylphenyl)diazen-1-yl]-4-[(2-methylphenyl)methyl]piperazine;
1-[(2-methylphenyl)methyl]-4-[(E)-2-phenyldiazen-1-yl]-4-piperazine; and
methyl 4-[(E)-2-[4-(2-phenylethyl)piperazin-1-yl]diazen-1-yl]benzoate.

7. A pharmaceutical composition comprising the compound of claim 1 and a pharmaceutically acceptable carrier.

8. The compound of claim 6, wherein the compound is 4-[(E)-2-(4-phenylpiperazin-1-yl)diazen-1-yl]benzonitrile.

9. The compound of claim 6, wherein the compound is methyl 4-[(E)-2-(4-phenylpiperazin-1-yl)diazen-1-yl]benzoate.

10. The compound of claim 6, wherein the compound is 1-[(E)-2-(4-methylphenyl)diazen-1-yl]-4-phenylpiperazine.

11. The compound of claim 6, wherein the compound is 1-[(E)-2-(4-nitrophenyl)diazen-1-yl]-4-phenylpiperazine.

* * * * *